United States Patent [19]

Bourgoin et al.

[11] Patent Number: 5,068,383

[45] Date of Patent: Nov. 26, 1991

[54] CATALYZED REDISTRIBUTION OF POLYORGANOSILOXANES

[75] Inventors: Jodi A. Bourgoin, Florence; Steven K. Freeburne, Edgewood, both of Ky.; Roland L. Halm, Madison, Ind.; Brian M. Naasz, LaGrange, Ky.; David S. Niswonger, Prospect, Ky.; Dennis G. VanKoevering, Florence, Ky.

[73] Assignee: Dow Corning Corporation, Midland, Mich.

[21] Appl. No.: 611,216

[22] Filed: Nov. 9, 1990

[51] Int. Cl.$^5$ .................................................. C07F 7/08
[52] U.S. Cl. ...................................... 556/452; 556/460
[58] Field of Search ................................. 556/452, 460

[56] References Cited

U.S. PATENT DOCUMENTS

| | | | |
|---|---|---|---|
| 2,421,653 | 6/1947 | Saur | 556/452 |
| 2,911,427 | 11/1959 | Brown | 556/452 |
| 3,065,252 | 11/1962 | Brown | 556/452 |
| 3,101,361 | 7/1963 | Brown | 556/452 |
| 3,162,662 | 12/1964 | Brown et al. | 556/452 |
| 3,549,680 | 12/1970 | Wegehaupt et al. | 556/452 |
| 3,642,851 | 2/1972 | Bennett | 556/452 |
| 3,646,088 | 2/1972 | Bakassian et al. | 556/452 |
| 4,073,801 | 2/1978 | Moretto et al. | 556/452 X |
| 4,113,760 | 9/1978 | Frey et al. | 556/452 |
| 4,329,482 | 5/1982 | Elskeikh | 556/452 X |
| 4,329,483 | 5/1982 | Speier | 556/452 X |

OTHER PUBLICATIONS

Concise Encyclopedia of Chemical Technology, John Wiley and Sons, NY, 1985, pp. 772-774.

*Primary Examiner*—Paul F. Shaver
*Attorney, Agent, or Firm*—William F. Boley

[57] ABSTRACT

The instant invention is a catalyzed process for the redistribution of linear, chloride or hydroxy end-terminated polyorganosiloxanes or cyclic polyorganosiloxanes. Effective catalysts for the described process are alumina, silica-alumina, activated carbon, zeolite, and acid clay. The catalyzed redistribution process can be incorporated as an element of a three-stage process. The three-stage process allows control of the yield of cyclic polyorganosiloxanes.

44 Claims, 1 Drawing Sheet

5,068,383

CATALYZED REDISTRIBUTION OF POLYORGANOSILOXANES

BACKGROUND OF INVENTION

The instant invention is a catalyzed process for the redistribution of linear, chloride or hydroxy end-terminated polyorganosiloxanes or cyclic polyorganosiloxanes. In an additional embodiment of the instant invention, the catalyzed redistribution process is part of a three-stage process for producing high yields of cyclic polyorganosiloxanes. Effective catalysts for the described processes are alumina, silica-alumina, activated carbon, zeolite, and acid clay.

Current industrial processes for the manufacture of silicone fluids, resins, and rubbers typically require as starting materials either hydroxy end-terminated linear polyorganosiloxanes or cyclic polyorganosiloxanes. These polysiloxanes can be produced by the hydrolysis of lower molecular weight polyorganohalosiloxanes and diorganodihalosilane. This process results in a polydispersed mixture of cyclic and linear polyorganosiloxanes. Separation of this polydispersed mixture, to isolate a desired linear or cyclic fraction, results in an excess of either linear or cyclic materials, as well as materials of undesired molecular weight. Therefore, a process which allows for converting linears to cyclics and vice-versa and allows for adjustment of molecular weight of polyorganosiloxane chains is desirable to allow recovery of these excess siloxanes.

Known methods for enhancing the production of cyclic polyorganosiloxanes include cracking of the polyorganosiloxanes, which is capital intensive; vacuum hydrolysis, which has poor enhancement capabilities; and aqueous hydrolysis, which tends to sacrifice chloride recovery. Other methods for enhancing the production of cyclic polyorganosiloxanes require the addition of solvents or surfactants, which makes recovery of the product more difficult and can compromise product purity.

There are many reports in the patent literature dealing with redistribution of polyorganosiloxanes in the presence of halosilanes or a halogen substituted siloxane and a catalyst. Sauer, U.S. Pat. No. 2,421,653, issued June 3, 1947, describes a process for effecting reaction between a hydrocarbon-substituted polysiloxane and a halosilane. The process may be run at an elevated temperature in the presence of a catalyst such as a hydrogen halide, or at room temperature in the presence of a hydrogen halide catalyst and an iron halide.

Brown, U.S. Pat. No. 3,065,252, issued Nov. 20, 1962, describes the reaction of halosilanes or halosiloxanes with organosiloxanes in the presence of catalysts, such as aminoalkyl-substituted organosilicon compounds, salts of monocarboxylic acids and aminoalkyl-substituted organosilicon compounds.

Brown, U.S. Pat. No. 3,101,361, issued Aug. 20, 1963, describes the interaction of a silane or silicone containing at least one halogenated silicon atom per molecule with a siloxane in the presence of catalysts such as aliphatic hydrocarbon amines, salts of monocarboxylic acid, and aliphatic hydrocarbon amines and an organic solvent.

Brown et al., U.S. Pat. No. 3,162,662, issued Dec. 22, 1964, describes a process for preparing linear chlorosiloxanes by reacting a halosilicon compound with cyclotrisiloxane in the presence of catalysts such as amines, amine salts of monocarboxylic acid and quaternary ammonium halides, amides, alkali metal halides, and ammonium salts of monocarboxylic acids; and inert organic solvents.

Wegehaupt et al., U.S. Pat. No. 3,549,680, issued Dec. 22, 1970, describes a process for preparing organohalogenosilicon compounds by reacting halogenosilicon compounds with organosiloxanes free of halogen bonded silicon, in the presence of phosphonitrile halides and organonitrogen derivatives of phosphorous acid or phosphoric acid.

Bennett, U.S. Pat. No. 3,642,851, issued Feb. 15, 1972, describes a process for preparing linear halosiloxane polymers through the redistribution of halosiloxanes or a halosiloxane with cyclotrisiloxane or cyclotetrasiloxane in the presence of phosphine oxides or amine oxides.

Bakassian et al., U.S. Pat. No. 3,646,088, issued Feb. 29, 1972, discloses conducting a redistribution reaction between a siloxane and a chlorosilane in the presence of hexalkylphosphotriamide.

Frey et al., U.S. Pat. No. 4,113,760, issued Sept. 12, 1978, describes a process comprising reacting a chlorosilane with organosiloxanes in the presence of activated charcoal. The organosiloxanes which were described for the process were cyclics of formula $(R_2SiO)_{n'}$, and linear organosiloxanes of formula $R_3SiO(R_2SiO)_mSiR_3$, where R represents hydrogen or the same or different monovalent hydrocarbon radicals and halogenated hydrocarbon radicals.

The present processes offer advantages over previously described processes. The present processes can be used not only to enhance the production of cyclic polyorganosiloxanes, but also to control the cyclic content from about zero to greater than 90 weight percent of the product. The described catalysts improve the rate of redistribution while minimizing organic cleavage. Cyclic polyorganosiloxanes as well as linear, chloride or hydroxy end-terminated polyorganosiloxanes can easily be redistributed to more desirable chloride-end terminated polyorganosiloxanes of 2 to 5 siloxane units. In addition, no solvents or surfactants are required and the catalyst are readily available and easily separated from polyorganosiloxane products.

SUMMARY OF THE INVENTION

The instant invention is a catalyzed process for the redistribution of linear, chloride or hydroxy end-terminated polyorganosiloxanes and cyclic polyorganosiloxanes. In a first embodiment of the instant invention, monodispersed, linear, chloride end-terminated polyorganosiloxane polymers are contacted with a catalyst effective in redistributing the polyorganosiloxane polymers to a polydispersed mixture of chloride end-terminated polyorganosiloxanes. In a second embodiment of the instant invention, a polydispersed mixture of linear, chloride or hydroxy end-terminated polyorganosiloxanes or cyclic polyorganosiloxanes is redistributed with an organochlorosilane or a linear, chloride end-terminated polyorganosiloxane of a lower degree of polymerization. In a third embodiment of the instant invention, the catalyzed redistribution process is part of a three-stage process which provides for controlled yields of cyclic polyorganosiloxanes. Effective catalysts for the described processes are alumina, silica-alumina, activated carbon, zeolite, and acid clay.

Figure 1:
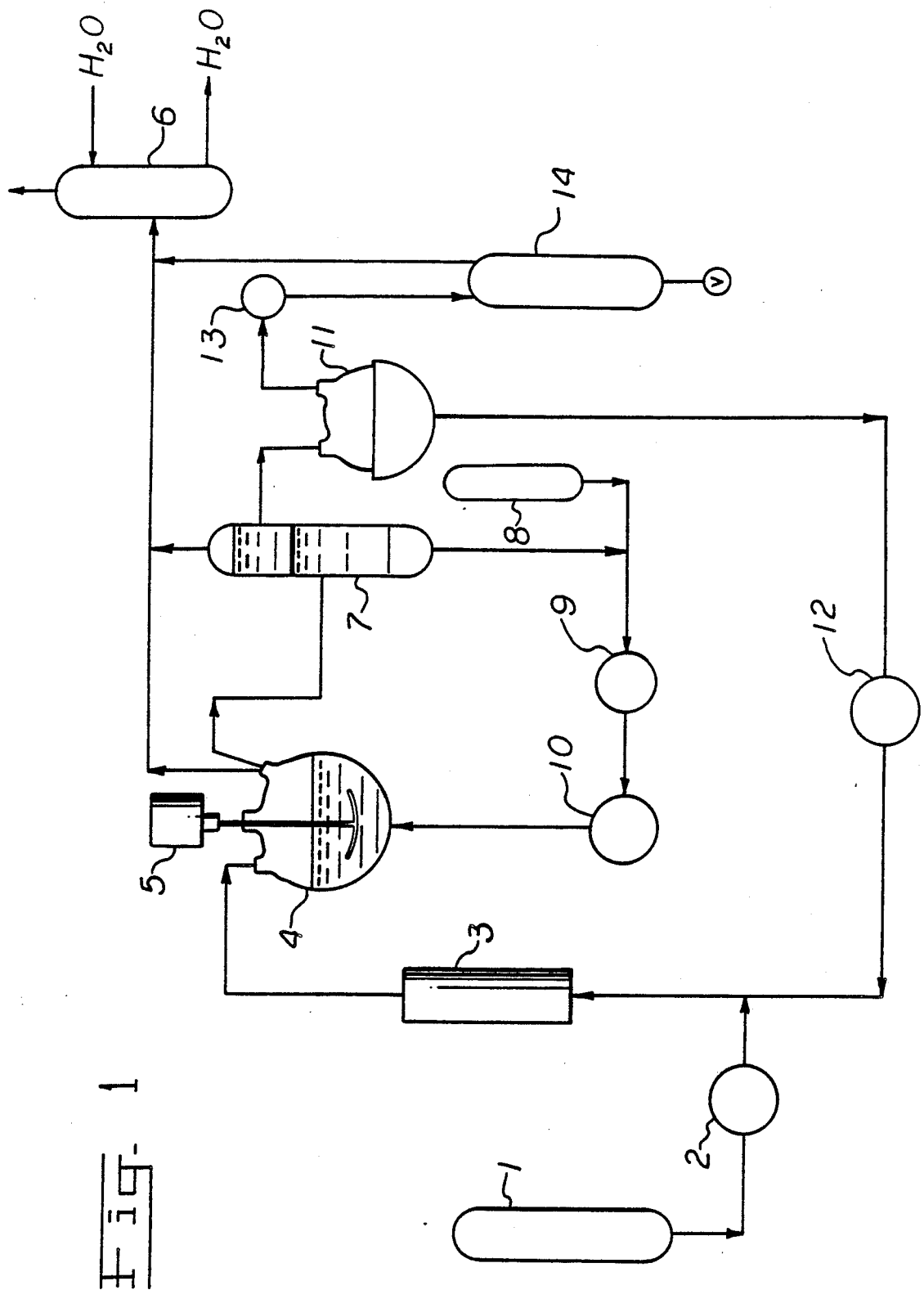
FIG. 1 illustrates the three-stage process described herein.

A column 3 is packed with a redistribution catalyst. The column 3 is connected to a reservoir 1 for feeding chlorosiloxanes to the column through a flow control device 2. Redistributed products from the column 3 are passed to a hydrolysis reactor 4, of a stirred-tank design, equipped with a stirring apparatus 5. Hydrogen chloride gas evolved in the hydrolysis reactor 4 is passed to a hydrogen chloride scrubber 6. Aqueous 36 weight percent hydrogen chloride is fed to the hydrolysis reactor 4 from a reservoir 8 through a metering device 9 and a hot oil bath 10, to provide make-up acid. The hot oil bath 10 heats the aqueous acid solution to compensate for heat lost from the evolution of hydrogen chloride gas. A portion of the reaction mixture is continuously withdrawn from the hydrolysis reactor 4 and passed to a phase separator 7. Within the phase separator, the hydrolysis mixture separates by gravity into an upper siloxane layer and a lower aqueous hydrogen chloride layer. The lower aqueous hydrogen chloride layer is withdrawn and recycled back to the hydrolysis reactor 4 along with aqueous make-up hydrogen chloride from reservoir 8 to maintain the interface level in the phase separator 7. The siloxane mixture is removed from the top of the phase separator 7 and passed to a flash distillation apparatus 11. The flash distillation apparatus is run under temperature and pressure conditions which cause cyclic polyorganosiloxanes and short-chain chloride end-terminated polyorganosiloxanes to be distilled out from higher molecular weight polyorganosiloxanes. The higher molecular weight materials are withdrawn from the bottom of the flash distillation apparatus 11 and recycled through flow regulator 12 to column 3. The distilled cyclic polyorganosiloxanes and short-chain, chloride end-terminated polyorganosiloxanes are withdrawn through regulator 13, condensed in water cooled condenser 14, and collected in a suitable container.

DESCRIPTION OF THE INVENTION

One embodiment of the instant invention is a process for the redistribution of monodispersed chloride end-terminated polyorganosiloxane polymers, hereinafter referred to as chlorosiloxanes, of formula

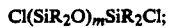

where each R is independently selected from a group consisting of hydrogen, and alkyl and substituted alkyl radicals of 1 to 6 carbon atoms; and m is an integer from 1 to 100. The process comprises contacting the chlorosiloxanes with a catalyst which facilitates redistribution of the chlorosiloxanes to a polydispersed mixture comprising chlorosiloxanes of formula

where R is as previously described. The polydispersed chlorosiloxane mixture comprises chlorosiloxanes with an average number of siloxane units (i.e., —$SiR_2O$—) denoted by the term m', where m' is equivalent to m.

The monodispersed chlorosiloxane polymers, to be redistributed, have a chloride atom on each end of the polymer chain. The presence of these reactive end-terminal chloride atoms are necessary for the present processes to operate efficiently. By monodispersed, it is meant the chlorosiloxane consists of 90 percent or greater, by weight, of chlorosiloxane polymers having the same value for m. The chlorosiloxanes are further substituted with independently chosen substituents, R, selected from a group consisting of hydrogen atoms, and alkyl and substituted alkyl radicals of 1 to 6 carbon atoms. The alkyl radical can be, for example, methyl, ethyl, propyl, isopropyl, butyl, isobutyl, tertbutyl, sec-butyl, pentyl or hexyl. Preferred is when each R is independently selected from the group consisting of hydrogen atoms and methyl. Most preferred is when R is methyl. The substituted alkyl radicals can be of the general formula $C_nH_{2n+1-a}X_a$, where n is an integer from one to six, the value a is an integer from 1 to $2n+1$, and x is a halogen. The preferred halogen is fluorine. The substituted alkyl radical can be, for example, 3,3,3-trifluoropropyl. When the substituted alkyl radical is 3,3,3-trifluoropropyl, it is preferred that R be independently selected from the group consisting of 3,3,3-trifluoropropyl and methyl. The value m can be any integer between 1 and 100. The preferred value for m is an integer from 4 to 25. It is preferred to apply the process to chlorosiloxane where all the R radicals are methyl.

The monodispersed chlorosiloxanes can be prepared by vacuum distillation or supercritical fluid extraction of polydispersed mixtures of chlorosiloxanes.

The monodispersed chlorosiloxanes are contacted with a catalyst which facilitates redistribution of the chlorosiloxanes to a polydispersed mixture of chlorosiloxanes. Contact of the catalyst with the chlorosiloxanes can be effected by standard means for contacting liquids with solids, for example, a batch process or a continuous-flow process. The process can be conducted, for example, in a fixed-bed, a stirred-bed, or a fluid-bed reactor.

The required contact time for the chlorosiloxanes with the catalyst, to effect redistribution, will depend upon such factors as temperature, type of chlorosiloxanes, and type of catalyst. In general, contact times between about one to 60 minutes have been found useful. Longer contact times may be employed, however, undesirable levels of organic cleavage from silicon may occur. Shorter contact times may result in inadequate redistribution of the chlorosiloxanes. A preferred contact time is about five to 15 minutes.

The process can be run at a temperature between about 0° C. and 200° C. Higher temperatures may be run, but these can result in unacceptable levels of organic cleavage from silicon atoms. A preferred temperature range is about 25° C. to 60° C.

The catalyst which facilitates redistribution of the monodispersed chlorosiloxanes to a polydispersed mixture of chlorosiloxanes is selected from a group consisting of alumina, silica alumina, zeolite, activated carbon, and acid clay. Silica-alumina refers to an amorphorus compound containing both silicon oxides and aluminum oxides. In general, the more silicon dioxide present the lower the catalytic activity of the silica-alumina. Preferred, is when the silica is less than about 30 weight percent of the silica alumina compound. The term "zeolite" refers to crystalline aluminosilicates of Group IA and Group IIA elements such as sodium, potassium, magnesium, and calcium. The zeolites effective in the process of the instant invention can be both synthetic and natural occurring zeolites, for example, as described in the Concise Encyclopedia of Chemical Technology, John Wiley and Sons, N.Y., 1985, pp. 772-774. A preferred zeolite is zeolite Y.

The catalyst can be carbon activated by treatment with anhydrous acid or chlorosilane. The catalytic activity of the activated carbon can be improved by bubbling gaseous hydrogen chloride through the carbon bed while conducting the redistribution processes described herein. The term "acid clay" refers to the class of naturally occurring layered silicate compounds that have been modified to obtain a controlled amount of residual acidity. The preferred catalyst is alumina.

It is preferred that the catalyst be free of water prior to contact with the chlorosiloxane. Water can be removed from the catalyst by, for example, a vacuum, heating, treating with gaseous hydrogen chloride, or treating with a chlorosilane.

The monodispersed chlorosiloxanes are redistributed to a polydispersed mixture of chlorosiloxanes of formula $Cl(SiR_2O)_mSiR_2Cl$, as previously described. By polydispersed, it is meant that chlorosiloxane polymers having differing numbers of siloxane units, m, are present in the mixture. The polydispersed chlorosiloxane mixture is distributed around an average value m', which is equivalent to m. By "equivalent," it is meant m' has an average value within a range of 80 percent to 120 percent of m.

A second embodiment of the instant process comprises:
(A) contacting a first polydispersed mixture comprising either
(1) chlorosiloxanes of formula $$Cl(SiR_2O)_xSiR_2Cl,$$

(2) hydroxysiloxanes of formula $$HO(SiR_2O)_xSiR_2OH,$$

(3) cyclic siloxanes of formula $(SiR_2O)_j$, or
(4) mixtures thereof;
where each R is independently selected from a group consisting of hydrogen, and alkyl and substituted alkyl radicals of 1 to 6 carbon atoms, x is a mean value of 1 to 5000, and j is a mean value of 3 to 50; with a second mixture in the presence of a catalyst; and
(B) forming a redistributed chlorosiloxane mixture.

Preferred is where the chlorosiloxanes and hydroxysiloxanes have an average value for x in the range of 7 to 1000. The preferred average value for j is in the range of 3 to 10. Preferred is when all the R radicals are methyl.

The first polydispersed mixture of siloxanes can be formed, for example, by hydrolysis of diorganodichlorosilane.

The second mixture comprises chlorosilanes, chlorosiloxanes, or a mixture thereof, of formula:

$$Cl(SiR_2O)_ySiR_2Cl,$$

where R is as previously described, y is a mean value of zero to less than x, when the first mixture comprises chlorosiloxanes or hydroxysiloxanes; and y is a mean value of zero to less than j, when the first mixture comprises cyclic siloxanes. Where the first mixture comprises a combination of chlorosiloxanes, hydroxysiloxanes, and cyclic siloxanes or any combination thereof, an average value for the number of siloxane units in all siloxanes present, $A_v$, can be determined and y chosen to fall in a range from 0 to less than $A_v$. The preferred value for y is zero. Preferred is where the second mixture comprises chlorosilanes and chlorosiloxanes on which all R radicals are methyl.

The redistributed mixture comprises chlorosiloxanes of formula $$Cl(SiR_2O)_zSiR_2Cl,$$

where R is as previously described; z is a mean value greater than y and less than x, when the first mixture is chlorosiloxanes; z is a mean value greater than y and less than x+2y when the first mixture is hydroxysiloxanes; z is a mean value greater than y and less than j, when the first mixture is cyclic siloxanes; and z is a mean value greater than y and less than $A_v'$, when the first mixture comprises a combination of chlorosiloxanes, hydroxysiloxanes, and cyclic siloxanes or any combination thereof. The value $A_v'$ is a mean value equal to $A_v$ plus the mole fraction of the hydroxysiloxane times 2y.

The first polydispersed mixture and the second mixture are contacted in the presence of a catalyst. Useful catalyst are those previously described. The preferred catalyst is alumina. The first and second mixtures may be combined and then fed to a reactor containing the catalyst or may be individually fed to a reactor containing the catalyst. The methods of contact of chlorosilanes with the catalyst are as previously described. A preferred contact method is a continuous flow fixed-bed reactor. The volume ratio of the second mixture to the first mixture can be varied to affect the value z of the redistributed chlorosilane mixture. As the ratio increases z approaches y. A preferred range for this ratio is about 0.1 to 30.

The described process forms a redistributed mixture comprising chlorosiloxanes of the general formula $Cl(SiR_2O)_mSiR_2Cl$, as previously described, with a mean value for the number of siloxane units, of z. The value z is greater than y and less than x, x+2y, j, or $A_v'$, depending upon the composition of the first mixture.

A third embodiment of the instant invention is a three-stage process comprising a redistribution, a hydrolysis, and a separation stage to produce cyclic siloxanes. A method for conducting this three-stage process is represented schematically in FIG. 1.

The process comprises contacting a first mixture comprising chlorosiloxanes of formula $Cl(SiR_2O)_xSiR_2Cl$, hydroxysiloxanes of formula $HO(SiR_2O)_xSiR_2OH$, cyclic siloxanes or formula $(SiR_2O)_j$, or any mixture thereof; as previously described, with a second mixture comprising chlorosilanes and chlorosiloxanes of formula $Cl(SiR_2O)_pSiR_2Cl$, where R is as previously described and p is an average value within a range of 0 to 7, in the presence of a catalyst which facilitates redistribution of chlorosiloxanes. A preferred value for x in the three-stage process is in the range of one to 100.

A redistributed mixture comprising chlorosiloxanes of formula $Cl(SiR_2O)_oSiR_2Cl$ is formed, where R is as previously described and o is an average value within the range of 0 to 7. The catalysts, process temperature, and contact times are as previously described. The method of contacting the first and second mixtures and the catalyst are as previously described.

The redistributed mixture of chlorosiloxanes is fed to a hydrolysis process where a hydrolysate is formed comprising cyclic siloxanes of formula $(R_2SiO)_q$, where q is an average value in a range of 3 to 25, chlorosiloxanes of formula $Cl(SiR_2O)_mSiR_2Cl$, and hydroxysiloxanes of formula $HO(SiR_2O)_xSiR_2OH$, as previously described. The hydrolysis reaction is run in the presence of stoichiometric or excess water in relation to the moles of chloride in the chlorosiloxanes to be redistributed. In general, the amount of excess water will be dictated by the method of chloride recovery, whether anhydrous or aqueous. The hydrolysis reaction can be run by standard methods, for example, in a continuous stirred tank reactor (CSTR), plug-flow reactor, fixed-bed reactor, or a fluidized-bed reactor.

In the third stage of the instant process, the cyclic siloxanes are separated from the chlorosiloxanes and hydroxysiloxanes. This separation can be effected by first causing a phase separation of the hydrolysate into an aqueous hydrogen chloride phase and a siloxane phase. Phase separation may be accomplished by gravitational methods such as settling or centrifugation. The recovered aqueous hydrogen chloride phase can be recycled to the hydrolysis reactor. The siloxane phase can then be separated into a desired cyclic siloxanes fraction and a chlorosiloxane/hydroxysiloxane fraction by standard means such as flash or column distillation or falling film evaporation. The chlorosiloxanes and hydroxysiloxanes are recycled to the redistribution reactor for redistribution to low molecular weight chlorosiloxanes capable of under going hydrolysis to cyclic polysiloxanes. The chlorosiloxanes and hydroxysiloxanes may be recycled on a continuous or batch basis. A volume ratio of the second chlorosilane or chlorosiloxane mixture to the recycled chlorosiloxanes and hydroxysiloxanes in the range of 1:1 to 100:1 has been found useful. The preferred ratio will depend upon the molecular weight of the recycled material, the composition of the second mixture, and the desired product. A preferred process is where p is zero, R is methyl, and the volume ratio of the second mixture to the recycled chlorosiloxanes is in the range of 1:1 to 30:1.

EXAMPLE 1

(Not within the scope of the instant invention) A mixture of dimethyldichlorosilane and chloride end-terminated polydimethylsiloxanes, with an average number of siloxane units of 28 per polymer chain, was allowed to react at room temperature for 147 hours. The molar ratio of dimethyldichlorosilane to polydimethylsiloxane was 25:1. The average number of siloxane units per polymer chain of the redistributed mixture was determined by supercritical fluid chromotography (SFC). The sampling times and the results are provided in Table 1.

TABLE 1

Redistribution of Chloride End-terminated Polysiloxane Polymers in The Absence of Catalyst.

| Time (h) | Polymer Length |
|---|---|
| 0 | 28.8 |
| 5 | 22.7 |
| 51 | 13.2 |
| 99 | 12.0 |
| 147 | 11.2 |

The data of Table 1 demonstrate that in the absence of a catalyst the chloride end-terminated polydimethylsiloxanes redistribute slowly.

EXAMPLE 2

Various materials were tested for their ability to catalyze the redistribution of a mixture of chloride end-terminated polydimethylsiloxanes and dimethyldichlorosilane (DMDCS). The test compounds were soaked overnight in DMDCS, at room temperature, to react away any water present in the catalyst. Chloride end-terminated polydimethylsiloxanes with an average number of siloxane units of approximately 26 were mixed with DMDCS at a molar ratio of 25 moles per mole of siloxane. This mixture of chloride end-terminated polydimethylsiloxanes and DMDCS was then contacted with the pretreated bed of catalyst for eight minutes, at a temperature of 40° C. to effect redistribution. The redistributed mixture was recovered and analyzed by SFC to determine the average molecular weight of the redistributed siloxanes.

Table 2 lists the type materials tested and the source of each material. Tested compounds, as listed in Table 2, were purchase from United Catalyst, Inc., Louisville, KY; Alfa Products, Danvers, MA; Norton, Akron, OH; Calgon, Pittsburg, PA; and Harshaw, Cleveland, OH.

The percent of linear chloride end-terminated polydimethylsiloxanes in the redistributed mixture less than 6 siloxane units in length is presented under the heading "% Linear<6." The value is calculated as a percent of all linear polydimethylsiloxanes in the redistributed mixture.

TABLE 2

Screening of Compounds as Catalysts For Redistribution of Chloride End-terminated Polydimethylsiloxanes

| Type Material | % Linears <6 | Source |
|---|---|---|
| Alumina | 96.3 | United Catalyst Inc. (CS331-1) |
| Silica-Alumina (8.4% SiO$_2$) | 93.3 | United Catalyst Inc. (L2271B) |
| Silica-Alumina (29% SiO$_2$) | 83.6 | United Catalyst Inc. (L2273B) |
| Y-Zeolite | 53.9 | Alfa Products |
| H-Mordenite | 4.9 | Norton |
| Erionite | 9.9 | United Catalyst Inc. |
| Activated Carbon | 32.0 | Calgon (BPL) |
| Acid Clay | 18.2 | Harshaw Filtrol |

The data presented in Table 2 demonstrate the ability of various materials to function as catalysts for the redistribution of a mixture of chloride end-terminated polydimethylsiloxanes and dimethyldichlorosilanes.

EXAMPLE 3

A series of runs was conducted to demonstrate that low molecular weight, chloride end-terminated polydimethylsiloxane polymers hydrolyze to cyclic siloxanes.

A continuous stirred-tank reactor (CSTR) was used. The reactor consisted of a 500 ml 3-neck flask equipped with a stirring paddle. The reactor contained a side nozzle from which hydrolysate was continuously removed. The hydrolysate was gravitationally phase separated in a separate vessel to a top siloxane phase and a bottom aqueous hydrogen chloride phase. The aqueous hydrogen chloride phase was recycled to the CSTR. Samples of the siloxane phase were collected for analysis by gas chromatography (GC) and SFC. The required heat for the reaction was provided by heating the recycled aqueous hydrogen chloride prior to returning to the CSTR.

A series of 11 baseline runs was conducted with DMDCS. These runs were conducted at 35° C., with a mixing speed of 600 rpm, a DMDCS feed rate of 12 ml per minute, and with added 42% weight percent aqueous hydrogen chloride.

In a second series of runs, monodispersed chloride end-terminated polydimethylsiloxane polymers (CEB$_s$, where s is the number of silicon atoms) were hydrolyzed. This series of runs was conducted at 35° C., with a mixing speed of 1100 rpm, a CEB$_s$ feed rate of 5 ml per minute, a DMDCS feed rate of 12 ml per minute, and with added 42% weight percent aqueous hydrogen chloride. The CEB$_s$ and DMDCS where fed separately into the bottom of the reactor.

The siloxane products from the reactor were analyzed by GC. The percent conversion of feed, DMDCS or CEB$_s$, to product was calculated using the following formula:

$$\% \text{ Conv} = \left[ \frac{\text{Wt \% Reactants in Feed} - \text{Wt \% Reactants in Product}}{\text{Wt \% Reactants in Feed}} \right] \times 100$$

The normalized percent cyclic yield was calculated from the GC or SFC data using the formula:

$$\% \text{ Cyclics} = \left[ \frac{\text{Wt \% Cyclics}}{\% \text{ Conv.}} \right] \times 100$$

The percent cyclics of a particular degree of polymerization (% D$_s$, where s is the number of silicon atoms in the ring) was calculated as:

$$\% D_s = \left[ \frac{\text{Wt \% } D_s}{\text{Wt \% Total Cyclics}} \right] \times 100$$

The data for these runs is presented in Table 3. The heading "feed" refers to the DMDCS or chloride end-terminated polydimethylsiloxane (CEB$_s$). The headings % D$_s$, % Conv., and % Cyclics are as described above.

TABLE 3

| | Linear Chloride End-terminated Polydimethylsiloxane Hydrolysis to Cyclic Polydimethylsiloxane | | | | | |
|---|---|---|---|---|---|---|
| | | | % D$_s$ | | | |
| Feed | % Conv | % Cyclics | D$_3$ | D$_4$ | D$_5$ | D$_6$ |
| DMDCS | 100 | 47 | 1 | 74 | 19 | 4 |
| CEB$_2$ | 100 | 43 | 1 | 72 | 20 | 5 |
| CEB$_3$ | 68 | 43 | 3 | 76 | 17 | 4 |
| CEB$_4$ | 55 | 65 | 0 | 96 | 3 | 1 |
| CEB$_5$ | 71 | 46 | 0 | 22 | 73 | 3 |
| CEB$_6$ | 49 | 12 | 0 | 25 | 21 | 53 |

The data presented in Table 3 demonstrate that linear chloride end-terminated polydimethylsiloxanes can be hydrolyzed to cyclic species and indicates that the distribution of the cyclics can be influenced by the chain length of the chloride end-terminated polydiorganosiloxane.

EXAMPLE 4

A hydrolysate containing high molecular weight (HMW) chloride end-terminated polydimethylsiloxanes with an average number of about 4000 siloxane units per polymer chain were redistributed with DMDCS. The hydrolysate was mixed with DMDCS at a volume ratio of 0.6:1 and passed through a column of alumina (United Catalysis, CS331-1) held at a temperature of 40° C. The resident time within the alumina bed was about 11.7 minutes. The product from the alumina column was collected and analyzed by SFC for size distribution of the siloxanes. The results are presented in Table 4. The heading "% HMWP" refers to the percent of chloride end-terminated polydimethylsiloxane in the feed or product mixture with an average number of siloxane units of about 4000. The heading "% Linears<6" refers to the percent of chloride end-terminated linears less than six siloxane units in length, as a percent of all linear polydimethylsiloxanes in the product or feed mixture.

TABLE 4

| | Redistribution of HMW Chloride End-terminated Polydimethylsiloxanes | |
|---|---|---|
| | % HMWP | % Linears < 6 |
| Feed | 1.2 | 0.6 |
| Product | <0.1 | 68.1 |

The data demonstrates the ability of alumina to effect redistribution of HMW chloride end-terminated polydimethylsiloxanes with dimethyldichlorosilane.

EXAMPLE 5

A three-stage process was run. In the first stage of the process, a mixture of chloride end-terminated polydimethylsiloxane polymers and DMDCS was redistributed in a plug-flow reactor. In the second stage of the process, the redistributed siloxane mixture was hydrolyzed in a CSTR reactor similar to that described in Example 3. In the third stage of the process, the hydrolysis mixture of stage 2 was separated into a cyclic siloxane portion and a linear siloxane portion by flash distillation. The linear siloxane portion was recycled back to the first stage of the process for further redistribution and conversion to cyclic siloxanes.

In the first stage of the process, a plug-flow reactor, of conventional design, with a packed bed of alumina (United Catalyst, Inc., CS331-1), was used to redistribute chloride end-terminated polydimethylsiloxanes with DMDCS to produce short chain, chloride end-terminated polydimethylsiloxanes. The alumina catalyst was initially soaked with DMDCS to remove water. After removal of residual water, additional DMDCS was continuously metered to the redistribution reactor at a rate of 6.5 to 7.0 ml per minute. Prior to entering the redistribution reactor, the DMDCS was combined with recycled bottom material from the stage 3 flas distillation procedure. The volume ratio of DMDCS to bottom material was maintained within the range of 2:1 to 3.1:1. Residence time of the feed materials within the packed bed of the redistribution reactor was approximately 8 minutes. Samples of the redistributed product were taken and analyzed using SFC.

In the second stage of the process, the short-chain chloride end-terminated polydimethylsiloxanes produced in the redistribution stage were hydrolyzed by continuous feeding to a CSTR similar to that described in Example 3. A co-feed of recycled 42% weight percent aqueous hydrogen chloride was fed to the CSTR along with the redistribution product. A volumetric ratio of approximate 4:1 acid to redistribution product was used. The liquid level in the CSTR was controlled at about 250 ml by withdrawing liquid from a side nozzle. The residence time of feed materials in the CSTR was about 5 minutes. Agitation of the mixture within the CSTR was provided by a stirring paddle rotated at 600 rpm. The CSTR reactor was held at 60° C. by heating the recycled aqueous hydrogen chloride prior to returning to the reactor. The hydrogen chloride gas generated by the reaction was vented at near atmospheric pressure directly to a standard vent scrubber.

The liquid hydrolysis products were continuously taken off the side nozzle of the CSTR and allowed to phase separate in a separate vessel. The bottom phase, consisting of aqueous hydrogen chloride, was recycled to the CSTR. The top phase, containing a mixture of siloxanes, was fed directly to a flash stripper. The interface level in the phase separator was maintained by feeding 36% weight percent aqueous hydrogen chloride to the separator to replenish the water used in the reaction. Samples of the siloxane product were taken and analyzed by GC and SFC.

In the third phase of the process the siloxane mixture, separated from the CSTR process, was fed directly into a 3 liter flash distillation vessel. The distillation vessel was a single-stage flash distillation apparatus operating at a temperature between 230° C. and 250° C. and at near atmospheric pressure. The cyclic siloxanes were distilled off, condensed, and collected. The liquid level in the distillation vessel was maintained by adjusting a bottoms take-off pump rate to give a liquid hold up time of approximate 30 minutes. The entire bottoms stream was recycled back to the stage 1 redistribution reactor for chain shortening. Samples of the distillate and the bottom products were taken and analyzed by SFC.

The three-stage process was run continuously over a two day period. The averaged results for samples collected over this time period are presented in Table 4. The data under the heading "% CEB1-5" is a summation of DMDCS and chloride end-terminated polydimethylsiloxane polymers of 1 to 4 siloxane units in length, present in the sample, as a weight percent of the total sample. The headings "% Cyclics" and "% Conv" are as previously described. The heading "% Cyclic Yield" is calculated as:

$$\% \text{ Cyclic Yield} = \left[ \frac{\text{WT \% Cyclics}}{\% \text{ Conv}/100} \right] \times 100.$$

The results are presented in Table 5.

TABLE 5

| Stage | % CEB1-5 | % Cyclics | % Conv | % Cyclic Yield |
|---|---|---|---|---|
| 1 | 96.3 | 0.7 | — | — |
| 2 | 12.5 | 41.3 | 88.9 | 48.4 |
| 3 (overheads) | 16.7 | 75.3 | — | —3 |
| Bottoms) | 4.9 | 22.1 | — | — |

The data of Table 5 demonstrate the ability to achieve efficient operation of a three-stage process for producing cyclic siloxanes, where non-volatile cyclics and chloride end-terminated polydimethylsiloxane linears are recycled to the process.

What is claimed is:

1. A process for the redistribution of chlorosiloxanes, the process comprising:
   (A) contacting a monodispersed mixture comprising chlorosiloxanes of formula $Cl(SiR_2O)_mSiR_2Cl$ where each R is independently selected from a group consisting of hydrogen, and alkyl and substituted alkyl radicals of one to six carbon atoms, and m is an integer from one to 100; with a catalyst which facilitates redistribution of the chlorosiloxane, the catalyst selected from a group consisting of alumina, silica-alumina, activated carbon, zeolite, and acid clay; and
   (B) forming a polydispersed redistributed mixture comprising chlorosiloxanes of formula $Cl(SiR_2O)_{m'}SiR_2Cl$, where R is as previously described and m' is a mean value equivalent to m.

2. A process according to claim 1, where the catalyst is alumina.

3. A process according to claim 1, where R is methyl.

4. A process according to claim 1, where each R is a radical independently selected from a group consisting of methyl and 3,3,3-trifluoropropyl.

5. A process according to claim 1, where each R is independently selected from a group consisting of hydrogen atoms and methyl.

6. A process according to claim 1, where m is an integer from four to 25.

7. A process according to claim 1, where the process is conducted at a temperature of about 25° C. to 60° C.

8. A process according to claim 1, where R is methyl and the catalyst is alumina.

9. A process for the redistribution of chlorosiloxanes, the process comprising:
   (A) contacting a first polydispersed mixture comprising chlorosiloxanes of formula $Cl(SiR_2O)_xSiR_2Cl$, where each R is independently selected from a group consisting of hydrogen, alkyl and substituted alkyl radicals of one to six carbon atoms, and x is a mean value of one to 5000, with a second mixture comprising chlorosilanes and chlorosiloxanes of formula $Cl(SiR_2O)_ySiR_2Cl$, where R is as previously described and y is a mean value of zero to less than x; in the presence of a catalyst which facilitates redistribution of chlorosiloxanes, the catalyst selected from a group consisting of alumina, silica-alumina, activated carbon, zeolite, and acid clay; and
   (B) forming a redistributed mixture comprising chlorosiloxanes of formula $Cl(SiR_2O)_zSiR_2Cl$, where R is as previously described and z is a mean value greater than y and less than x.

10. A process according to claim 9, where the catalyst is alumina.

11. A process according to claim 9, where R is methyl.

12. A process according to claim 9, where each R is independently selected from a group consisting of methyl and 3,3,3-trifluoropropyl radicals.

13. A process according to claim 9, where each R is independently selected from a group consisting of hydrogen atoms and methyl.

14. A process according to claim 9, where x is seven to 1000 and y is zero.

15. A process according to claim 9, where the process is conducted at a temperature of about 25° C. to 60° C.

16. A process according to claim 9, where the catalyst is alumina and R is methyl.

17. A process according to claim 9, where the catalyst is alumina, R is methyl, x is seven to 1000, and y is zero.

18. A process for the redistribution of hydroxysiloxanes, the process comprising:
(A) contacting a first polydispersed mixture comprising hydroxysiloxanes of formula $$HO(SiR_2O)_xSiR_2OH,$$

where each R is independently selected from a group consisting of hydrogen, alkyl and substituted alkyl radicals of one to six carbon atoms, and x is a mean value of one to 5000, with a second mixture comprising chlorosilanes and chlorosiloxanes of formula $$Cl(SiR_2O)_ySiR_2Cl,$$

where R is as previously described and y is a mean value of zero to less than x; in the presence of a catalyst which facilitates redistribution of chlorosiloxanes, the catalyst selected from a group consisting of alumina, silica-alumina, activated carbon, zeolite, and acid clay; and
(B) forming a redistributed mixture comprising chlorosiloxanes of formula $$Cl(SiR_2O)_zSiR_2Cl,$$

where R is as previously described and z is a mean value greater than y and less than x+2y.

19. A process according to claim 18, where the catalyst is alumina.

20. A process according to claim 18, where R is methyl.

21. A process according to claim 18, where each R is independently selected from a group consisting of methyl and 3,3,3-trifluoropropyl radicals.

22. A process according to claim 18, where each R is independently selected from a group consisting of hydrogen atoms and methyl.

23. A process according to claim 18, where x is seven to 1000 and y is zero.

24. A process according to claim 18, where the process is conducted at a temperature of about 25° C. to 60° C.

25. A process according to claim 18, where the catalyst is alumina and R is methyl.

26. A process according to claim 18, where the catalyst is alumina, R is methyl, x is seven to 1000, and y is zero.

27. A process for the redistribution of cyclic siloxanes, the process comprising:
(A) contacting a first polydispersed mixture comprising cyclic siloxanes of formula $$(SiR_2O)_j,$$

where each R is independently selected from a group consisting of hydrogen, alkyl and substituted alkyl radicals of one to six carbon atoms, and j is a mean value of three to 50, with a second mixture comprising chlorosilanes and chlorosiloxanes of formula $$Cl(SiR_2O)_ySiR_2Cl,$$

where R is as previously described and y is a mean value of zero to less than j; in the presence of a catalyst which facilitates redistribution of chlorosiloxanes, the catalyst selected from a group consisting of alumina, silica-alumina, zeolite, and acid clay; and
(B) forming a redistributed mixture comprising chlorosiloxanes of formula $$Cl(SiR_2O)_zSiR_2Cl,$$

where R is as previously described and z is a mean value greater than y and less than j.

28. A process according to claim 27, where the catalyst is alumina.

29. A process according to claim 27, where R is methyl.

30. A process according to claim 27, where each R is independently selected from a group consisting of hydrogen atoms and methyl.

31. A process according to claim 27, where j is 3 to 10 and y is zero.

32. A process according to claim 27, where the process is conducted at a temperature of about 25° C. to 60° C.

33. A process according to claim 27, where the catalyst is alumina and R is methyl.

34. A process according to claim 27, where the catalyst is alumina, R is methyl, j is 3 to 10, and y is zero.

35. A three-stage process for preparing cyclic siloxanes, the process comprising:
(A) contacting a first mixture comprising chlorosiloxanes of formula $$Cl(SiR_2O)_xSiR_2Cl,$$

where each R is independently selected from a group consisting of hydrogen atoms, and alkyl and substituted alkyl radicals of one to six carbon atoms and x is a mean value of one to 5000; with a second mixture comprising chlorosilanes and chlorosiloxanes of formula $$Cl(SiR_2O)_pSiR_2Cl,$$

where R is as previously described and p is a mean value of zero to 7; in the presence of a catalyst which facilitates redistribution of chlorosiloxanes;
(B) forming a redistributed mixture comprising chlorosiloxanes of formula $$Cl(SiR_2O)_oSiR_2Cl$$

where R is as previously described and o is a mean value within a range of greater than zero and less than seven;
(C) hydrolyzing the redistributed mixture of chlorosiloxanes to form a hydrolysate comprising cyclic siloxanes of formula $(R_2SiO)_q,$ where R is as previously described and q is a mean value of three to 25, and chlorosiloxanes;

(D) separating the cyclic siloxanes from the chlorosiloxanes; and (E) recycling the chlorosiloxanes as a feed to step (A).

36. A process according to claim 35, where the catalyst is selected from a group consisting of alumina, silicaalumina, zeolite, activated carbon, and acid clay.

37. A process according to claim 35, where the catalyst is alumina.

38. A process according to claim 35, where R is methyl.

39. A process according to claim 35, where each R is independently selected from a group consisting of hydrogen atoms and methyl.

40. A process according to claim 35, where the catalyst is alumina and R is methyl.

41. A process according to claim 35, where the contacting of the first mixture and the second mixture with the catalyst occurs at a temperature of about 25° C. to 60° C.

42. A process according to claim 35, where hydrolysis of the redistributed mixture is conducted in a fixed-bed reactor.

43. A process according to claim 35, where separating the cyclic siloxanes from the chlorosiloxanes is effected by gravitational separation into a siloxane phase and an aqueous hydrogen chloride phase and the siloxane phase is flash distilled.

44. A process according to claim 35, where the catalyst is selected from a group consisting of alumina, silica-alumina, zeolite, and acid clay.

* * * * *